(12) United States Patent
Cummins

(10) Patent No.: US 9,974,678 B2
(45) Date of Patent: May 22, 2018

(54) WIRE COLLECTION DEVICE WITH VARYING COLLECTION DIAMETER

(71) Applicant: Cook Medical Technologies LLC, Bloomington, IN (US)

(72) Inventor: Sean Cummins, County Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 455 days.

(21) Appl. No.: 14/639,566

(22) Filed: Mar. 5, 2015

(65) Prior Publication Data

US 2015/0250631 A1 Sep. 10, 2015

Related U.S. Application Data

(60) Provisional application No. 61/950,493, filed on Mar. 10, 2014.

(51) Int. Cl.
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC .. A61F 2/95; A61F 2/966; A61F 2/962; A61F 2002/9517; A61F 2002/9511;
(Continued)

(56) References Cited

U.S. PATENT DOCUMENTS

| 706,606 A | 8/1902 | Spriggs |
| 2,939,680 A | 6/1960 | Powell |

(Continued)

FOREIGN PATENT DOCUMENTS

| EP | 1 251 796 B1 | 12/2004 |
| WO | WO 94/16762 A1 | 8/1994 |

(Continued)

OTHER PUBLICATIONS

Abbott Laboratories, "Absolute Pro® .035 Biliary Self-Expanding Stent System," obtained at internet address <http://www.abbotvascular.com/docs/ifu/peripheral_intervention/eIFU_absolute_pro_35_Billary_SelfExpanding_Stent_System.pdf>, EL2070955, dated Jul. 24, 2009, 11 pages.

*Primary Examiner* — Anh Dang
(74) *Attorney, Agent, or Firm* — Brinks Gilson & Lione

(57) ABSTRACT

A stent delivery system includes a wire collection device which is constructed with a thumbwheel coupled to a collection spindle that is rotatable to collect a retraction wire about a varying collection diameter of the collection spindle. A proximal end of an outer stent-constraining sheath is coupled to the collection spindle by the retraction wire and a distal end of the outer sheath retractably surrounds a distally-disposed self-expanding stent. The collection spindle includes a substantially constant outer diameter greater than the varying collection diameter, and the varying collection diameter increases from a first end of the spindle towards a second end of the spindle along a spiral groove formed between the varying collection diameter and the substantially constant outer diameter in a manner that provides substantially constant rotating force on the thumbwheel, thereby accommodating changing resistance as the outer sheath is retracted and releases binding force of the stent.

20 Claims, 11 Drawing Sheets

(58) Field of Classification Search
CPC ....... A61F 2002/9665; A61F 2002/011; B65G 23/06; B65G 23/04
See application file for complete search history.

(56) References Cited

U.S. PATENT DOCUMENTS

| | | | |
|---|---|---|---|
| 4,466,576 A | 8/1984 | Simson | |
| 4,483,326 A | 11/1984 | Yamaka et al. | |
| 5,026,377 A | 6/1991 | Burton et al. | |
| 5,534,007 A | 7/1996 | St. Germain et al. | |
| 5,772,669 A | 6/1998 | Vrba | |
| 5,904,667 A | 5/1999 | Falwell | |
| 5,968,052 A | 10/1999 | Sullivan, III et al. | |
| 6,059,813 A | 5/2000 | Vrba et al. | |
| 6,238,402 B1 | 5/2001 | Sullivan, III et al. | |
| 6,273,895 B1 | 8/2001 | Pinchuk et al. | |
| 6,387,977 B1 | 5/2002 | Sawhney et al. | |
| 6,520,983 B1 | 2/2003 | Colgan et al. | |
| 6,607,551 B1 | 8/2003 | Sullivan et al. | |
| 6,660,031 B2 | 12/2003 | Tran et al. | |
| 6,773,446 B1 | 8/2004 | Dwyer et al. | |
| 6,805,314 B2 | 10/2004 | Hopper | |
| 6,860,898 B2 | 3/2005 | Stack et al. | |
| 6,884,259 B2 | 4/2005 | Tran et al. | |
| 6,905,461 B2 | 6/2005 | Hino | |
| 6,939,352 B2 | 9/2005 | Buzzard et al. | |
| 7,052,511 B2 | 5/2006 | Weldon et al. | |
| 7,122,050 B2 | 10/2006 | Randall et al. | |
| 7,300,438 B2 | 11/2007 | Falwell et al. | |
| 7,300,456 B2 | 11/2007 | Andreas et al. | |
| 7,604,611 B2 | 10/2009 | Falwell et al. | |
| 7,615,042 B2 | 11/2009 | Beyar et al. | |
| 7,674,282 B2 | 3/2010 | Wu et al. | |
| 7,758,625 B2 | 7/2010 | Wu et al. | |
| 7,815,669 B2 | 10/2010 | Matsuoka et al. | |
| 7,935,141 B2 | 5/2011 | Randall et al. | |
| 7,967,829 B2 | 6/2011 | Gunderson et al. | |
| 7,976,574 B2 | 7/2011 | Papp | |
| 7,993,384 B2 | 8/2011 | Wu et al. | |
| 8,025,692 B2 | 9/2011 | Feeser | |
| 8,075,606 B2 | 12/2011 | Dorn | |
| 8,216,296 B2 | 7/2012 | Wu et al. | |
| 8,323,326 B2 | 12/2012 | Dorn et al. | |
| 2003/0163085 A1 | 8/2003 | Tanner et al. | |
| 2004/0006380 A1 | 1/2004 | Buck et al. | |
| 2004/0087979 A1* | 5/2004 | Field | A61B 17/0469 606/148 |
| 2005/0033403 A1 | 2/2005 | Ward et al. | |
| 2005/0256452 A1 | 11/2005 | DeMarchi et al. | |
| 2005/0256562 A1 | 11/2005 | Clerc et al. | |
| 2005/0273151 A1 | 12/2005 | Fulkerson et al. | |
| 2007/0055340 A1 | 3/2007 | Pryor | |
| 2007/0088421 A1 | 4/2007 | Loewen | |
| 2007/0168014 A1 | 7/2007 | Jimenez et al. | |
| 2007/0191925 A1 | 8/2007 | Dorn | |
| 2007/0219617 A1 | 9/2007 | Saint | |
| 2008/0188920 A1 | 8/2008 | Moberg et al. | |
| 2008/0300574 A1 | 12/2008 | Belson et al. | |
| 2008/0319387 A1 | 12/2008 | Amisar et al. | |
| 2009/0024133 A1 | 1/2009 | Keady et al. | |
| 2009/0099641 A1 | 4/2009 | Wu et al. | |
| 2009/0125093 A1 | 5/2009 | Hansen | |
| 2009/0210046 A1 | 8/2009 | Shumer et al. | |
| 2009/0270969 A1 | 10/2009 | Fargahi et al. | |
| 2010/0004606 A1 | 1/2010 | Hansen et al. | |
| 2010/0036472 A1* | 2/2010 | Papp | A61F 2/95 623/1.11 |
| 2010/0049297 A1 | 2/2010 | Dorn | |
| 2010/0076541 A1 | 3/2010 | Kumoyama | |
| 2010/0137967 A1 | 6/2010 | Atlani et al. | |
| 2010/0145431 A1 | 6/2010 | Wu et al. | |
| 2010/0168834 A1 | 7/2010 | Ryan et al. | |
| 2010/0174290 A1 | 7/2010 | Wüebbeling et al. | |
| 2011/0295354 A1 | 12/2011 | Bueche et al. | |
| 2012/0022635 A1 | 1/2012 | Yamashita | |
| 2012/0041537 A1 | 2/2012 | Parker et al. | |
| 2012/0059448 A1 | 3/2012 | Parker et al. | |
| 2012/0101562 A1 | 4/2012 | Gunderson et al. | |
| 2012/0123516 A1 | 5/2012 | Gerdts et al. | |
| 2012/0143304 A1 | 6/2012 | Wüebbeling et al. | |
| 2012/0158117 A1 | 6/2012 | Ryan | |
| 2012/0296409 A1 | 11/2012 | Kawakita | |
| 2013/0013047 A1 | 1/2013 | Ramos et al. | |

FOREIGN PATENT DOCUMENTS

| | | |
|---|---|---|
| WO | WO 2006/014233 A2 | 2/2006 |
| WO | WO 2007/022395 A1 | 2/2007 |
| WO | WO 2007/044929 A1 | 4/2007 |
| WO | WO 2008/034793 A1 | 3/2008 |
| WO | WO 2008/124844 A1 | 10/2008 |
| WO | WO 2008/134104 A2 | 11/2008 |
| WO | WO 2010/120671 A1 | 10/2010 |

\* cited by examiner

| $F_t$ | 8mm | 9mm | 10mm | 11mm | 12mm | 13mm | 14mm | 20mm |
|---|---|---|---|---|---|---|---|---|
| 1 | 0.004 | 0.0045 | 0.005 | 0.0055 | 0.006 | 0.0065 | 0.007 | 0.01 |
| 2 | 0.008 | 0.009 | 0.01 | 0.011 | 0.012 | 0.013 | 0.014 | 0.02 |
| 3 | 0.012 | 0.0135 | 0.015 | 0.0165 | 0.018 | 0.0195 | 0.021 | 0.03 |
| 4 | 0.016 | 0.018 | 0.02 | 0.022 | 0.024 | 0.026 | 0.028 | 0.04 |
| 5 | 0.02 | 0.0225 | 0.025 | 0.0275 | 0.03 | 0.0325 | 0.035 | 0.05 |
| 6 | 0.024 | 0.027 | 0.03 | 0.033 | 0.036 | 0.039 | 0.042 | 0.06 |
| 7 | 0.028 | 0.0315 | 0.035 | 0.0385 | 0.042 | 0.0455 | 0.049 | 0.07 |
| 8 | 0.032 | 0.036 | 0.04 | 0.044 | 0.048 | 0.052 | 0.056 | 0.08 |
| 9 | 0.036 | 0.0405 | 0.045 | 0.0495 | 0.054 | 0.0585 | 0.063 | 0.09 |
| 10 | 0.04 | 0.045 | 0.05 | 0.055 | 0.06 | 0.065 | 0.07 | 0.1 |
| 11 | 0.044 | 0.0495 | 0.055 | 0.0605 | 0.066 | 0.0715 | 0.077 | 0.11 |
| 12 | 0.048 | 0.054 | 0.06 | 0.066 | 0.072 | 0.078 | 0.084 | 0.12 |
| 13 | 0.052 | 0.0585 | 0.065 | 0.0715 | 0.078 | 0.0845 | 0.091 | 0.13 |
| 14 | 0.056 | 0.063 | 0.07 | 0.077 | 0.084 | 0.091 | 0.098 | 0.14 |
| 15 | 0.06 | 0.0675 | 0.075 | 0.0825 | 0.09 | 0.0975 | 0.105 | 0.15 |
| 16 | 0.064 | 0.072 | 0.08 | 0.088 | 0.096 | 0.104 | 0.112 | 0.16 |
| 17 | 0.068 | 0.0765 | 0.085 | 0.0935 | 0.102 | 0.1105 | 0.119 | 0.17 |
| 18 | 0.072 | 0.081 | 0.09 | 0.099 | 0.108 | 0.117 | 0.126 | 0.18 |
| 19 | 0.076 | 0.0855 | 0.095 | 0.1045 | 0.114 | 0.1235 | 0.133 | 0.19 |
| 20 | 0.08 | 0.09 | 0.1 | 0.11 | 0.12 | 0.13 | 0.14 | 0.2 |
| 21 | 0.084 | 0.0945 | 0.105 | 0.1155 | 0.126 | 0.1365 | 0.147 | 0.21 |
| 22 | 0.088 | 0.099 | 0.11 | 0.121 | 0.132 | 0.143 | 0.154 | 0.22 |
| 23 | 0.092 | 0.1035 | 0.115 | 0.1265 | 0.138 | 0.1495 | 0.161 | 0.23 |
| 24 | 0.096 | 0.108 | 0.12 | 0.132 | 0.144 | 0.156 | 0.168 | 0.24 |
| 25 | 0.1 | 0.1125 | 0.125 | 0.1375 | 0.15 | 0.1625 | 0.175 | 0.25 |
| 26 | 0.104 | 0.117 | 0.13 | 0.143 | 0.156 | 0.169 | 0.182 | 0.26 |
| 27 | 0.108 | 0.1215 | 0.135 | 0.1485 | 0.162 | 0.1755 | 0.189 | 0.27 |
| 28 | 0.112 | 0.126 | 0.14 | 0.154 | 0.168 | 0.182 | 0.196 | 0.28 |
| 29 | 0.116 | 0.1305 | 0.145 | 0.1595 | 0.174 | 0.1885 | 0.203 | 0.29 |
| 30 | 0.12 | 0.135 | 0.15 | 0.165 | 0.18 | 0.195 | 0.21 | 0.3 |
| 31 | 0.124 | 0.1395 | 0.155 | 0.1705 | 0.186 | 0.2015 | 0.217 | 0.31 |
| 32 | 0.128 | 0.144 | 0.16 | 0.176 | 0.192 | 0.208 | 0.224 | 0.32 |
| 33 | 0.132 | 0.1485 | 0.165 | 0.1815 | 0.198 | 0.2145 | 0.231 | 0.33 |
| 34 | 0.136 | 0.153 | 0.17 | 0.187 | 0.204 | 0.221 | 0.238 | 0.34 |

FIG. 11B

WIRE COLLECTION DEVICE WITH VARYING COLLECTION DIAMETER

RELATED APPLICATION

This application claims priority to U.S. provisional application No. 61/950,493 filed Mar. 10, 2014, which is incorporated by reference herein in its entirety.

TECHNICAL FIELD

Embodiments disclosed in the present application relate generally to wire collection devices for providing a mechanical advantage in a stent delivery system.

BACKGROUND

Current delivery systems for self-expanding stents generally employ "pin and pull" systems that include an inner catheter extending through an outer sheath. Typically, the stent is placed inside the outer sheath and held in a compressed position by the outer sheath as the outer sheath and inner catheter are inserted into a patient's body vessel. To deploy the stent, the user retracts, or pulls, the outer sheath using one hand while the other hand holds the inner catheter stationary to maintain position of the stent as the outer sheath is retracted, thereby allowing the stent to gradually expand as the outer sheath uncovers the stent.

In these "pin and pull" systems, the user has difficulty maintaining the position of the inner catheter while pulling on the outer sheath because of resistance between the inner catheter and outer sheath, between the outer sheath and the stent, and between the outer sheath and the surrounding vascular walls, or other surrounding blood vessel or body vessel. To overcome this resistance, the user may need to exert a large amount of force that leads to various complications, including for example, inaccurate stent positioning, displacement of the stent, shortening or lengthening of the stent, or other damage to the structure of the stent, or damage to the target vessel.

"Pin and pull" systems may also have other disadvantages, including, for example, lack of control during stent deployment and requirement of assistance from a second person. The resistance between the outer sheath and stent varies as more of the stent is uncovered and the stent expands. Specifically, the stent's self-expanding outward circumferential bias frictionally binds it against the outer sheath. During sheath retraction, this binding force decreases as the stent is released, which correspondingly decreases the retraction force needed on the outer sheath. Thus, stent deployment may be difficult to control because the required deployment force varies as the outer sheath retracts across the surface of the stent. As a result, the user must vary the force applied to the outer sheath and the inner catheter in order to maintain a steady deployment speed and ensure accurate stent placement. In most pin and pull systems, the ratio of handle movement to stent deployment distance is 1:1, requiring the user to move faster to deploy longer stents and increasing difficulty in controlling the stent. Because the user's hands are holding the distal ends of the outer sheath and inner catheter, the user cannot easily monitor or attend to the positioning of the outer sheath in the hemostasis valve to ensure accurate stent placement, such that an assistant must be present to attend to the positioning of the outer sheath in the hemostasis valve and accurate positioning of the stent.

Other vascular stent placement delivery systems offer one-handed operation by converting hand-movements into indexed movement of the outer sheath. Such systems generally still operate, however, with a 1:1 ratio of handle movement to stent deployment distance. In other words, such systems do not provide mechanical advantage to accommodate, or reduce the amount of work required for, deployment of longer stents as compared to deployment of shorter stents.

BRIEF SUMMARY

In one aspect, a stent delivery system includes a wire collection device with a thumbwheel, a collection spindle, and a retraction wire. The thumbwheel is coupled to the collection spindle and rotation of the thumbwheel actuates rotation of the collection spindle to collect the retraction wire around a varying collection diameter. The retraction wire is coupled to an outer sheath or cannula that holds or surrounds a stent, such as a self-expanding stent. An inner catheter or cannula extends through the outer sheath and positions the stent as the outer sheath is retracted to uncover and deploy the stent. The collection spindle has a substantially constant outer diameter and a varying collection diameter that increases or decreases from a first end of the spindle to a second end of the spindle. The retraction wire collects around the collection spindle along a spiral groove formed between the varying collection diameter and the substantially constant outer diameter. The varying collection diameter is configured to provide a substantially constant rotating force on the thumbwheel, accommodate changing resistance force as the outer sheath is retracted, and release binding force between the stent and the outer sheath.

In another aspect, a stent delivery system includes a wire collection device with two or more collection spindles that have varying collection diameters and substantially constant outer diameters. The spindles are coupled, directly or indirectly, to a thumbwheel, so that turning or rotating the thumbwheel causes the spindles to rotate to collect retraction wires around the spindles. The retraction wires collect along a groove that forms between the varying collection diameter and the substantially constant outer diameter. The retraction wires are also coupled, directly or indirectly, to an outer sheath or cannula that is retracted to uncover or deploy a stent.

In another aspect, a wire collection device for a stent delivery system includes a pair of collection spindles that rotate to collect a pair of retraction wires around the varying collection diameters of the collection spindles. The retraction wires are coupled, directly or indirectly, to an outer sheath or cannula that is retracted to uncover or deploy a stent. The spindles also have grooves formed between the varying collection diameters and substantially constant outer diameters of the collection spindles, so that the retraction wires collect along the grooves of the spindles as the spindles rotate. The spindles are coupled to a thumbwheel that, when turned or rotated, causes the spindles to rotate and collect the retraction wires.

Other systems, methods, features, and advantages of the disclosure will be, or will become, apparent to one with skill in the art upon examination of the following figures and detailed description. It is intended that all such additional systems, methods, features and advantages be included within this description, be within the scope of the invention, and be protected by the claims.

BRIEF DESCRIPTION OF THE DRAWINGS

FIG. 11B is a table showing torque variation for an exemplary wire collection device for a stent delivery system.

DETAILED DESCRIPTION

Figure 1A:
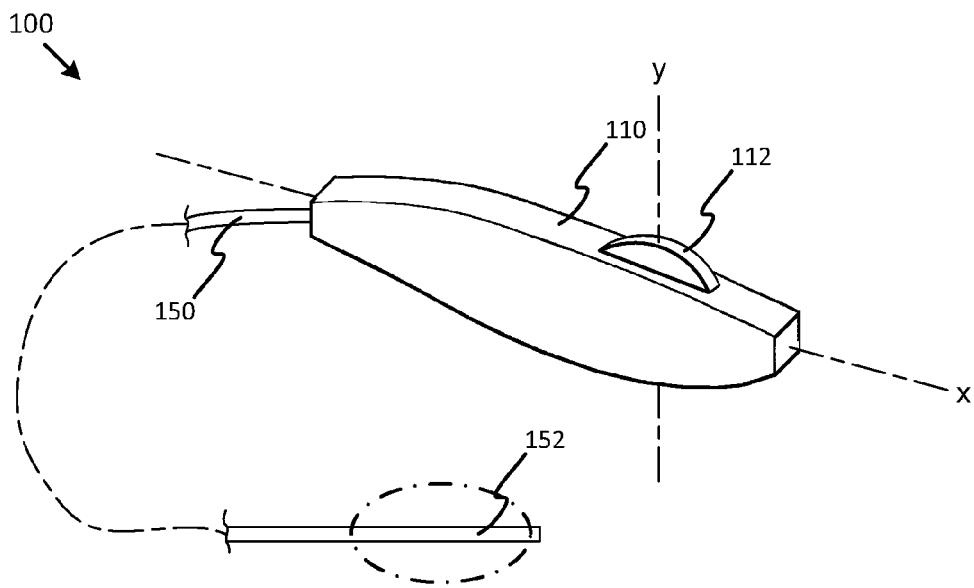
FIG. 1A is a view of an exemplary wire collection device for a stent delivery system.
Figure 1B:
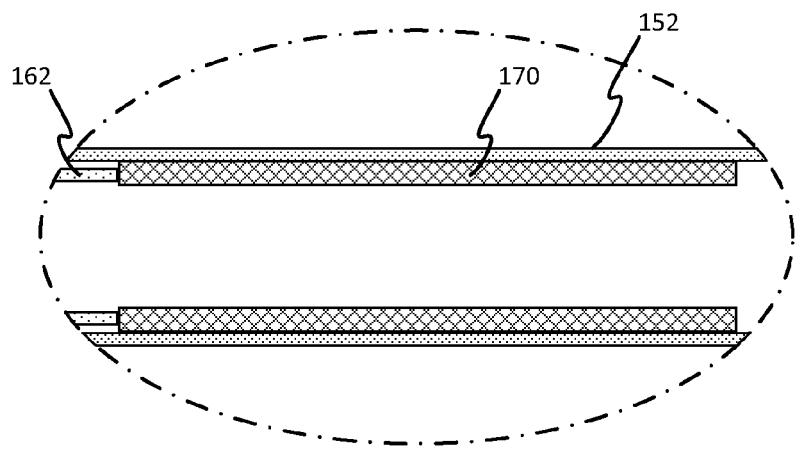
FIG. 1B is a diagrammatic illustration of a detailed cross-sectional view of an exemplary wire collection device for a stent delivery system.
Figure 1C:
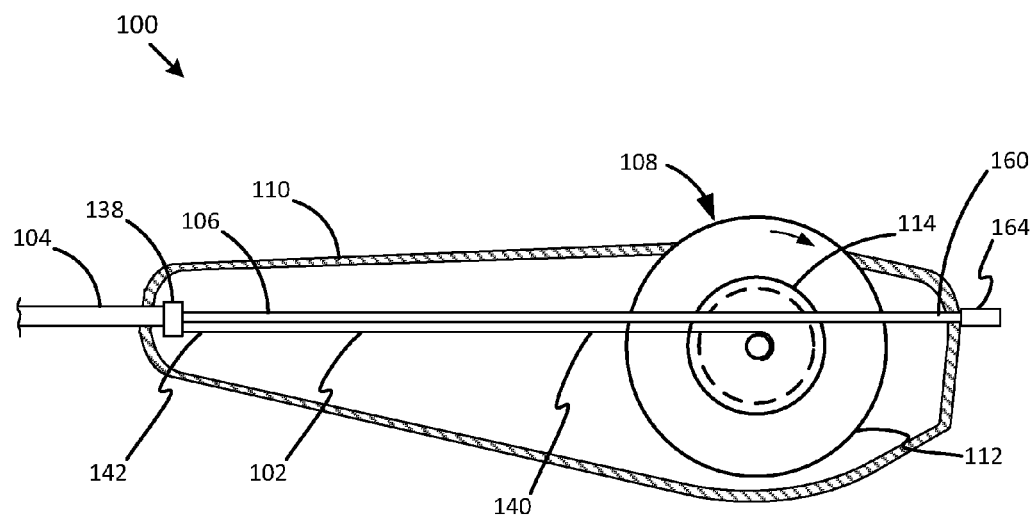
FIG. 1C is a diagrammatic longitudinal cross-sectional illustration of an exemplary wire collection device for a stent delivery system.

Various embodiments are described below with reference to the drawings. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

A wire collection device for a stent delivery system is provided in some embodiments. The stent delivery system includes a retraction wire that is attached at a proximal end to a wire collection device, which is rotatable to pull and collect the retraction wire around a collection spindle with varying collection diameter. The wire collection device includes a thumbwheel and the collection spindle with varying collection diameter. A user may retract the outer sheath by turning the thumbwheel to pull and collect the retraction wire around the collection diameter. The system may include one or more retraction wires connected to the proximal end of the outer sheath, and one or more collection spindles with varying collection diameters, each collecting one or more retraction wires around the varying collection diameters.

A distal end of the retraction wire is connected or attached to a proximal end of an outer sheath that holds a stent at or near a distal end of an inner catheter. The inner catheter extends through the outer sheath from a proximal end near the wire collection device to a distal end near the stent. The stent and the distal ends of the inner catheter and outer sheath are inserted into a body vessel until the stent is located at a desired location. As the thumbwheel is turned, the wire collection device pulls and collects the retraction wire around the collection spindle, thereby retracting the outer sheath across the inner catheter to uncover the stent while the inner catheter holds the stent in the desired location. The stent may be a self-expanding stent, or a stent that is expanded by the force of a balloon.

The terms "outer sheath" and "inner catheter," as used herein, mean a tube, cannula, or other similar structure, that may have solid, woven, braided, porous, smooth, or other type of wall with one or more apertures extending through all or part of the structure. As used herein, "retraction wire" means a rope, cord, wire, cable, belt, chain, or any other strand(s) of material that is suitable for use in a stent delivery system to retract or pull an outer sheath, or cannula, to allow stent deployment or delivery. The term "collection spindle," as used herein, means one or more axles, spindles, or generally cylindrical structures around which the retraction wire is wound or collected. The wire collection device may be used with one or more retraction wires, and may include one or more collection spindles. As used herein, "collection diameter" refers to the diameter around which a retraction wire collects or is wound. Thus, the "collection diameter" may increase as the retraction wire overlaps itself as it is being collected, or wound, around an axle, spindle, collection drum, or other cylindrical structure.

When the wire collection device is used with a self-expanding stent, the required deployment force may be greater during initial deployment of the stent and may decrease as the outer sheath, or cannula, begins to move and/or uncovers more of the stent. As used herein, "required deployment force" refers to an amount of force required to overcome the frictional forces between the outer sheath and the stent, frictional forces between the outer sheath and an inner catheter, or cannula, that holds the stent in place as the outer sheath is retracted, and frictional forces between the outer sheath and the surrounding body vessels where the stent is being implanted or placed.

The wire collection device may provide the user of the stent delivery system with a more consistent "touch and feel" by reducing the variation in applied force, or the amount of force applied by the user, to deploy the stent. As used herein, the term "applied force" means the amount of force applied to the wire collection device by the user. For example, the applied force may be the amount of force applied to turn the thumbwheel and generate the required deployment force. In some embodiments, the applied force may result from a user pressing a thumb against thumbwheel and flexion of the thumb causes the thumbwheel to turn and activate retraction of the sheath. The pressure or force that is perceived, or felt, by the user may be referred to as the perceived thumb flexion force. Reducing variation in the required applied force may be accomplished by varying the mechanical advantage provided to the user as the required stent deployment force increases, where the mechanical advantage of the wire collection device is determined by the ratio of the thumbwheel diameter to collection diameter. More particularly, the mechanical advantage increases as the collection diameter increases relative to the diameter of the thumbwheel. The collection spindle and varying collection diameter may be sized and configured to control the degree and rate of change in the mechanical advantage provided during stent deployment. As the retraction wire collects around a larger collection diameter, the stent deployment distance increases for the same amount of rotation of the thumbwheel.

The wire collection device may provide a mechanical advantage such that the deployment distance, or retraction distance of the outer sheath, increases with hand movements of the user or revolutions of the thumbwheel. The wire collection device controls retraction of the outer sheath so as to improve user feel and control for accurately positioning the stent. The wire collection device may be configured so that the user may exert a steady, or consistent, applied force throughout the deployment despite variation in the force required to retract the outer sheath or deploy the stent. The wire collection device may provide a mechanical advantage to the user that results in a 1:1 ratio, or greater than or less than a 1:1 ratio, of handle movement to stent deployment distance. The gear ratio may be configured according to variation in the required deployment force, the diameter of the thumbwheel, and type of stent.

In some embodiments, as illustrated with reference to FIGS. 1A-C and 2A-B, a stent delivery system 100 includes a retraction wire 102 coupled to an outer sheath 104, an inner catheter 106 extending through the outer sheath 104, a wire collection device 108, and a handle 110 housing the wire collection device 108. For example, the handle 110 may have a length of about 100 mm and a height of about 40 mm-50 mm. The proximal end 140 of the retraction wire is attached to the collection spindle 114. The distal end 142 of the retraction wire 102 may be attached, directly or indirectly, to a proximal end 150 of the outer sheath 104 and at or near a proximal end 160 of the inner catheter 106. The proximal end 160 of the inner catheter 106 is fixed to the handle 110. The distal end 152 of the outer sheath 104 retractably surrounds a stent 170 located at or near a distal end 162 of the inner catheter 106. The wire collection device 108 includes a thumbwheel 112 and a collection spindle 114.

Figure 2A:
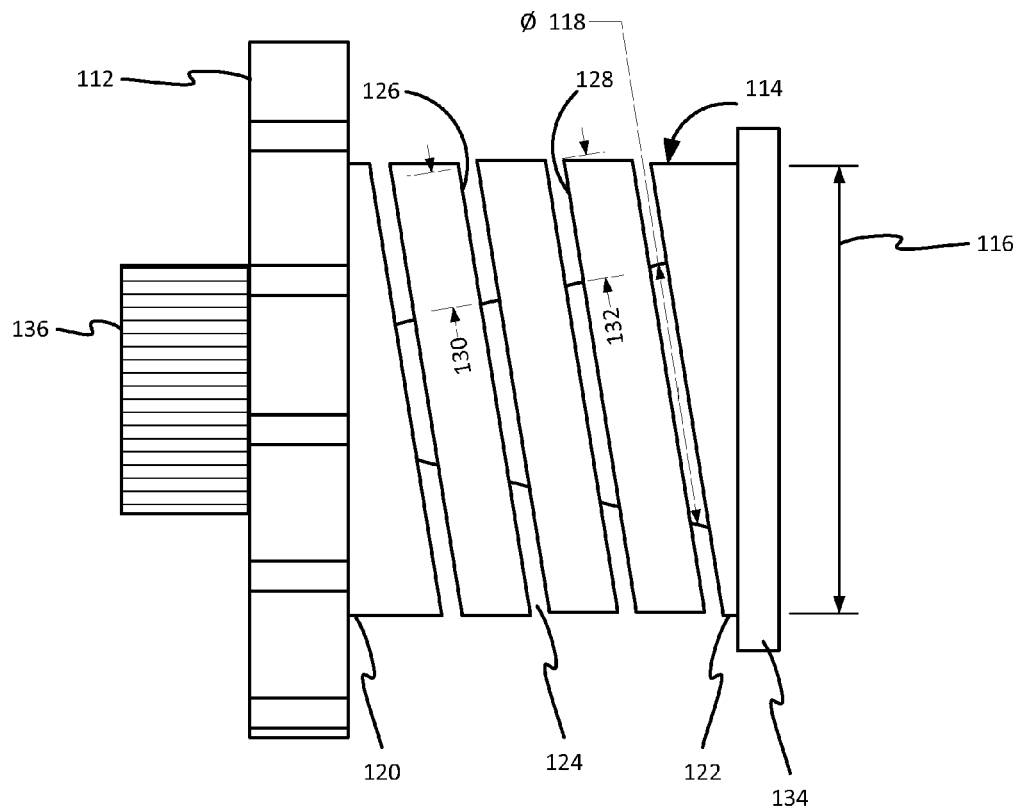
FIG. 2A is a diagrammatic illustration of an exemplary wire collection device for a stent delivery system.

With reference to FIG. 2A, the spindle 114 has a substantially constant outer diameter 116 and a varying collection diameter 118 that increases from a first end 120 to a second end 122 of the spindle 114. A spiral groove 124 is formed between the varying collection diameter 118 and the substantially constant outer diameter 116 of the spindle 114. As used herein, the term "spiral groove" refers to a cutout that runs along an outer diameter, or outer surface of a collection spindle from end to end or partially along the height of the spindle, and is not limited to regularly shaped spirals. Walls 126, 128 define lateral sides of the spiral groove, and the heights 130, 132 of the walls 126, 128 vary with the varying collection diameter 118. For example, the heights 130, 132 may vary according to the difference between the outer diameter 116 and the varying collection diameter 118 at a location along the spindle 114.

The collection diameter 118 may vary to accommodate a required deployment force profile, e.g., rate and degree that the deployment force changes during sheath retraction. For example, as illustrated with reference to FIG. 2A, the collection diameter 118 may increase from the end 120 of the spindle 114 nearer the thumbwheel 112 towards the free end 122 of the spindle 114. In some embodiments, the collection diameter 118 may increase from the free end 122 of the spindle 114 towards the end 120 of the spindle 114 nearer the thumbwheel 112. In some embodiments, the retraction wire 102 is attached to an end of the spindle 114 with the smaller collection diameter, so that collection of the retraction wire 102 begins at the smaller collection diameter and the collection diameter 118 increases as the thumbwheel 112 is turned. Thus, the retraction wire 102 collects along the spiral groove 124 towards the end of the spindle 114 with the larger diameter, and the collection diameter 118 increases as the outer sheath 104 is retracted. In some embodiments, the retraction wire 102 is attached to an end of the spindle 114 with the larger collection diameter, so that collection of the retraction wire begins at the larger collection diameter, and the collection diameter 118 decreases as the outer sheath 104 is retracted. Thus, the spiral groove 124 guides the retraction wire 102 from the larger collection diameter towards the end of the spindle 114 with the smaller collection diameter, and the collection diameter 118 decreases throughout the stent deployment process. Collection of the retraction wire 102 may begin at the end 120 of the spindle 14 nearer the thumbwheel 112, or at the free end 122 of the spindle 114.

The collection diameter 118 may vary (e.g., increase or decrease) linearly or curvilinearly, or otherwise, to accommodate variation in the required deployment force. For example, the collection surface of the spiral groove may generally have the shape of a cone, ellipsoid, paraboloid, or hyperboloid, or a stepped or irregular shape. Those of skill in the art will appreciate that the changes in the required deployment force, or force required to retract the outer sheath 104, can be measured and predicted within general ranges. As such, the profile of the spiral groove 124 may be optimized in certain embodiments to provide a desired smooth deployment operation of the thumbwheel 112 for a user. The pitch of the spiral may remain consistent from end to end of the spindle 114, or the pitch may vary from end to end of the spindle 144.

In operation, turning or rotating the thumbwheel 112 actuates rotation of the collection spindle 114 so that the retraction wire 102 collects, or winds, around the varying collection diameter 118. The walls 126, 128 maintain the retraction wire 102 within the spiral groove 124 as the retraction wire 102 collects around the spindle 114. In this way, the wire collection device 108 may control the collection diameter of the retraction wire 102, so as to provide a substantially constant rotating force on the thumbwheel 112. The wire collection device 108 may also accommodate changing resistance as the outer sheath 104 is retracted and binding force of the stent to the outer sheath 104 is released. The spiral groove 124 may be configured to accommodate the distance that the outer sheath 104 is retracted to deploy the stent 170. Sheath retraction may be monitored, for example, by fluoroscopy, or with the use of radiopaque markers placed on the outer sheath 104 and inner catheter 106 that align when retraction is complete. In some embodiments, a lock or other mechanism may be configured to stop rotation of the thumbwheel 112 after a certain length of the retraction wire 102 has been collected.

In some embodiments, the wire collection device 108 includes a shoulder 134 that supports the spindle 114 in the housing of the handle 110. The wire collection device 108 may also include a ratchet 136 that allows the thumbwheel 112 to rotate in one direction and prevents rotation in the opposite direction. For example, when the user releases the thumbwheel 112, the ratchet 136 may prevent the retraction wire 102 from unwinding from the spindle 114. The ratchet 136 may be a pawl and gear ratchet located on or coupled to the thumbwheel 112. In some embodiments, the ratchet 136 may act directly on the retraction wire 102, for example, as with a cable tie or tie wrap. In some embodiments, the ratchet 136 may have a high friction surface that acts on the thumbwheel 112 to prevent the thumbwheel 112 from rotating in the opposite direction. The thumbwheel 112 and collection spindle 114 may be made of rubber, plastic, metal, ABS, polycarbonate, POM, PTFE, aluminium, glass-filled plastics, stainless steel or any combination thereof, or any other material that is sufficiently rigid to withstand the force required to turn the thumbwheel 112 and the required deployment force, and sufficiently lightweight for use in a surgical procedure.

Figure 10:
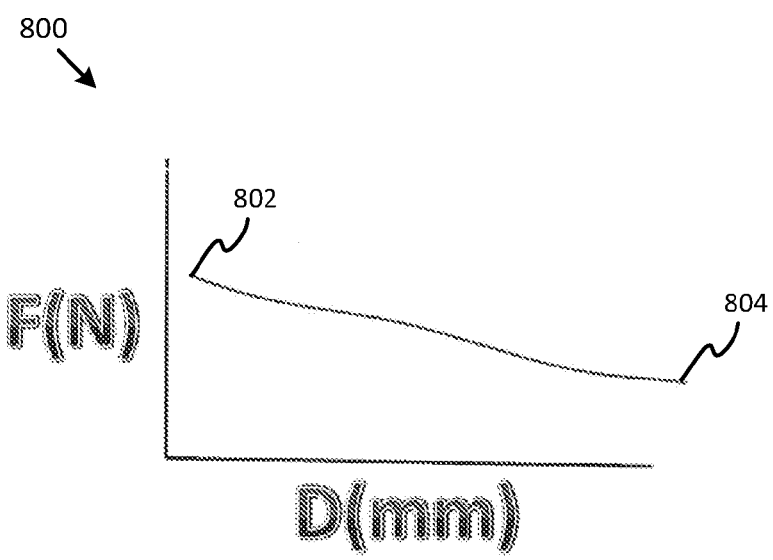
FIG. 10 is an applied force profile of a force variation curve for an exemplary wire collection device for a stent delivery system.

The initial required deployment force, or the amount of force required to begin retraction of the outer sheath 104, depends on the force required to overcome the frictional force (e.g., static friction) between the outer sheath 104 and the stent 170. The stent 170 may be located at or near a distal end 152 of the outer sheath 104 and a distal end 162 of the inner catheter 106. With reference to FIG. 10, the proximal end (not shown) of the inner catheter 106 may be held in place by a known mechanism, structure, or attachment, by the housing of the handle 110. The inner catheter 106 is shown truncated to maintain clear illustration of the thumbwheel, but in different embodiments, its proximal end will generally protrude through the housing of the handle 110 and may include a luer structure 164 for ease of attaching a fluid-delivery device (e.g., for delivering flushing fluid, radio-opaque contrast fluid, or other fluid), and it may also serve as a passage for a wire guide. As the outer sheath 104 begins to move, or retract, the required deployment force, or force required to continue retracting the outer sheath 104, decreases. The wire collection device 108 increases the mechanical advantage provided to the user as the collection diameter 118 increases. Therefore, the ratio of movement of the thumbwheel 112 to stent deployment distance decreases as the collection diameter increases. This may provide the user with a more consistent "feel" throughout the deployment of the stent.

Figure 2B:
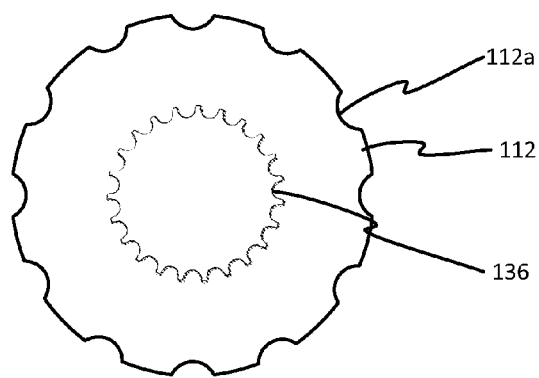
FIG. 2B is a diagrammatic illustration of a thumbwheel for an exemplary wire collection device for a stent delivery system.

With reference to FIG. 2B, the thumbwheel 112 may include notches 112a that provide grip to enable the user to turn the thumbwheel 112 more easily. In some embodiments, the thumbwheel 112 may have a rough, gritty, or cross-hatched contact surface, or may be covered by or made of material, such as rubber or silicon, that provide traction to the user. For example, the thumbwheel 112 may be formed by a two shot mold process, and/or may include materials containing acetyl or acrylonitrile butadiene styrene (ABS).

In some embodiments, for example with reference to FIG. 10, the retraction wire 102 is coupled to the outer sheath 104 by a sledge 138 that is within the housing of the handle 110. The inner catheter 106 extends through an aperture in the sledge 138. As the retraction wire 102 collects around the wire collection device 108, the outer sheath 104 and sledge 138 slide across the inner catheter 106, allowing the inner catheter 106 to maintain its position. In some embodiments, the retraction wire 102 may be coupled to the outer sheath 104, such as, for example, by embedding the retraction wire 102 in walls of the outer sheath 104 or welding the retraction wire 102 to the outer sheath 104. The proximal end 150 of the outer sheath 104 may extend into the housing of the handle 110, or may end outside of the housing of the handle 110.

Figure 3:
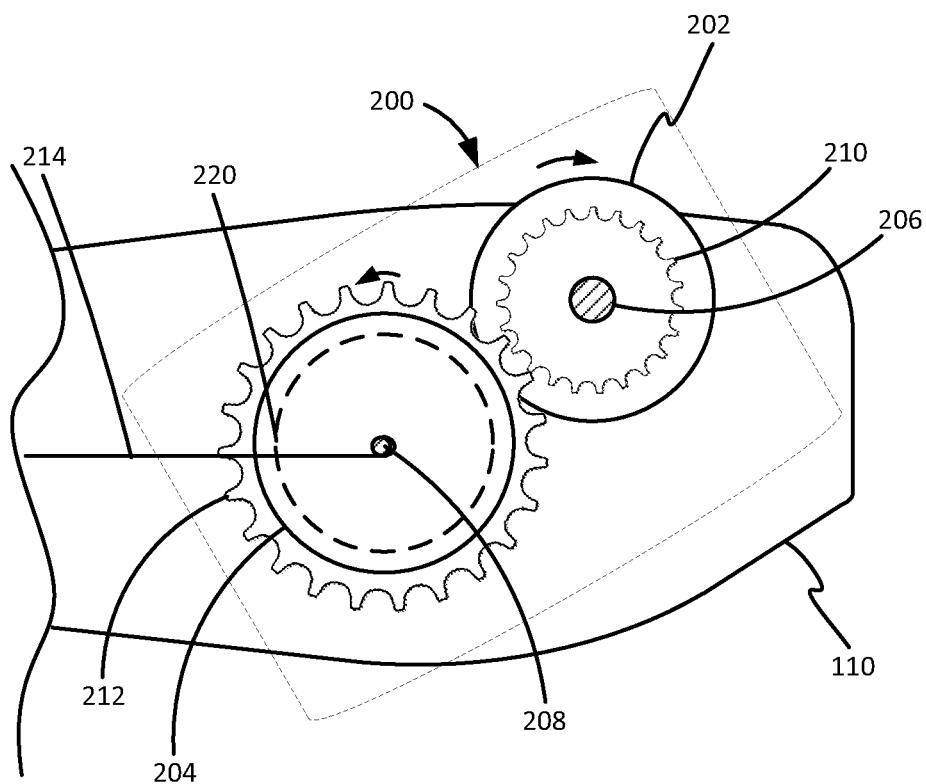
FIG. 3 is a diagrammatic longitudinal cross-sectional illustration of a partial view of an exemplary wire collection device for a stent delivery system.

In some embodiments, as illustrated with reference to FIG. 3, of a wire collection device 200 for a stent delivery system, the thumbwheel 202 may be offset from the collection spindle 204. For example, the thumbwheel 202 may be mounted on an axle 206 that is axially offset from the collection spindle 204 and axle 208. The thumbwheel 202 is coupled to the collection spindle 204, for example, by a transmission mechanism, such as mesh gears 210, 212. Mesh gear 210 may be formed or molded as part of the thumbwheel 202, or may be a separate component that is mounted on the axle 206. Mesh gear 212 may be formed or molded as part of the spindle 204, or may be a separate component that is co-axial with the spindle 204. The spindle 204 may have a diameter that is larger or smaller than the diameter of the thumbwheel 202. When the thumbwheel 202 rotates, gear 210 engages gear 212, thereby actuating rotation of the collection spindle 204 to collect the retraction wire 214 around the spindle 204. In other embodiments, the transmission mechanism may include a transmission belt, a rack and pinion, a clutch, a ratchet, or any combination thereof.

Figure 4:
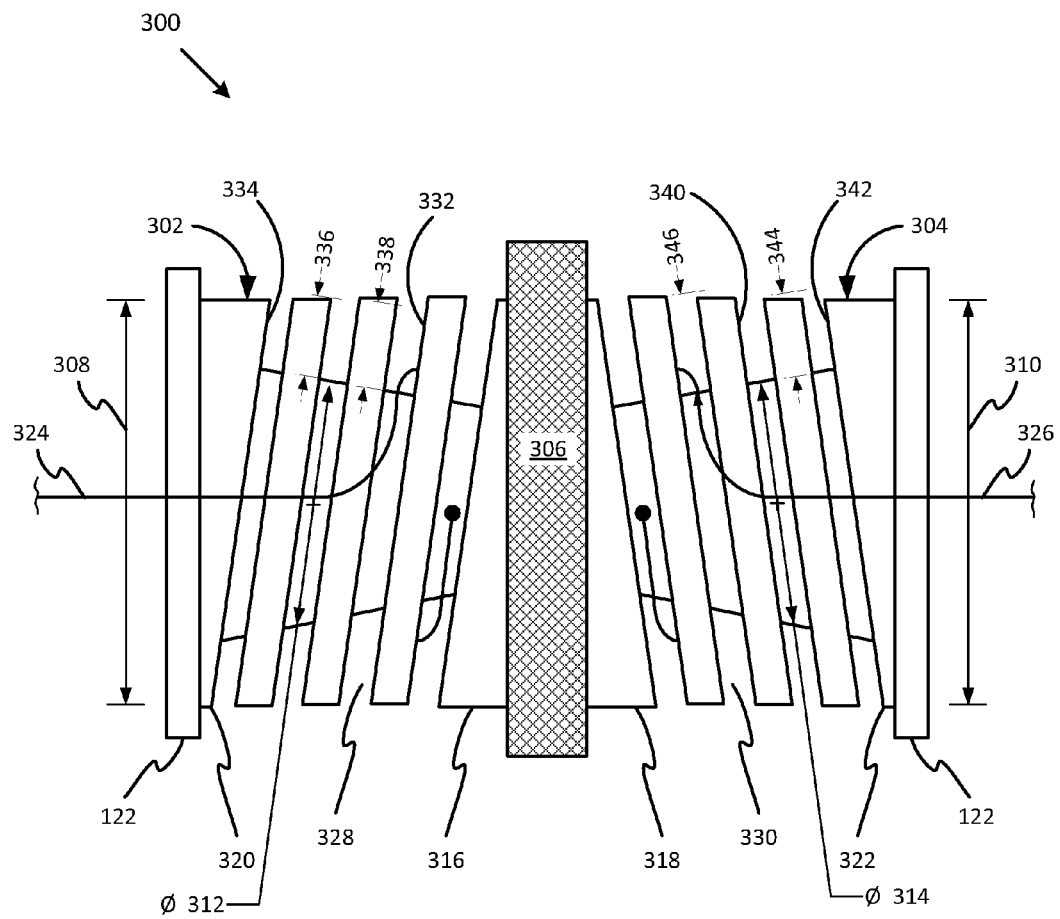
FIG. 4 is a diagrammatic illustration of an exemplary wire collection device for a stent delivery system.

In some embodiments, as illustrated with reference to FIG. 4, a wire collection device 300 may include a first collection spindle 302 and a second collection spindle 304, with a thumbwheel 306 between the two spindles 302, 304. The thumbwheel 306 may be co-axial or offset from the spindles 302, 304. The spindles 302, 304 may also be co-axial, or may be offset in relation to each other and/or the thumbwheel 306. The spindles 302, 304 each have substantially constant outer diameters 308, 310, and varying collection diameters 312, 314 that increase from a first end 316, 318 to a second end 320, 322 of the spindles 302, 304. The spindles 302, 304 are attached to retraction wires 324, 326 that are attached, directly (e.g., embedded in a wall) or indirectly (e.g., by a sledge or other known connector), to outer sheath 104. Spiral grooves 328, 330 are formed between the varying collection diameters 312, 314 and the substantially constant outer diameters 308, 310 of the spindles 302, 304. Walls 332, 334 define lateral sides of the spiral groove 328, and heights 336, 338 of the walls 332, 334 vary with the varying collection diameter 312. For example, heights 336, 338 may vary according to the difference between the outer diameter 308 and the varying collection diameter 312 at a location along the spindle 302. Walls 340, 342 define lateral sides of the spiral groove 330, and heights 344, 346 of the walls 340, 342 vary with the varying collection diameter 314. For example, heights 344, 346 may vary according to the difference between the outer diameter 310 and the varying collection diameter 314 at a location along the spindle 304.

Turning or rotation of the thumbwheel 306 actuates rotation of the collection spindles 302, 304 to collect, or wind, the retractions wires 324, 326 around the varying collection diameters 312, 314 of the spindles 302, 304. Walls 332, 334, 340, 342 may maintain or guide the retraction wires 324, 326 along the spiral grooves 328, 330. Maintaining or guiding the retraction wires 324, 326 along the grooves may prevent the retraction wires 324, 326 from kinking, overlapping, or experiencing any undesired tracking as they are collected around the spindles 302, 304, thus allowing the wire collection device 300 to accurately control sheath retraction speed and provide a smooth feel to the user. This feature, in this and other presently disclosed embodiments, may provide significantly improved control and precision over other wire-winding structures.

The collection diameters 312, 314 may vary to accommodate a required deployment force profile, e.g., rate and degree that the deployment force changes during sheath retraction. For example, as illustrated with reference to FIG. 4, the collection diameters 312, 314 may increase from ends 316, 318 of the spindles 302, 304 nearer the thumbwheel 306 towards free ends 320, 322 of the spindles 302, 304. In some embodiments, the collection diameters 312, 314 may decrease from ends of from ends 316, 318 of the spindles 302, 304 nearer the thumbwheel 306 towards free ends 320, 322 of the spindles 302, 304. Collection of retraction wires 324, 326 may begin at ends 316, 318 of the spindles 302, 304 nearer the thumbwheel 306, or at the free ends 320, 322 of the spindles 302, 304.

The collection diameters 312, 314 may vary (e.g., increase or decrease) linearly or curvilinearly. For example, the collection surface of the spiral groove may generally have the shape of a cone, ellipsoid, paraboloid, or hyperboloid, or a stepped or irregular shape. Those of skill in the art will appreciate that the changes in the required deployment force, or force required to retract the outer sheath 104, can be measured and predicted within general ranges. As such, the profile of the spiral grooves 328, 330 may be optimized in certain embodiments to provide a desired smooth deployment operation of the thumbwheel 306 for a user. The pitch of the spirals may remain consistent from end to end of the spindle 302, 304, or the pitch may vary from end to end of the spindles 302, 304.

Figure 5:
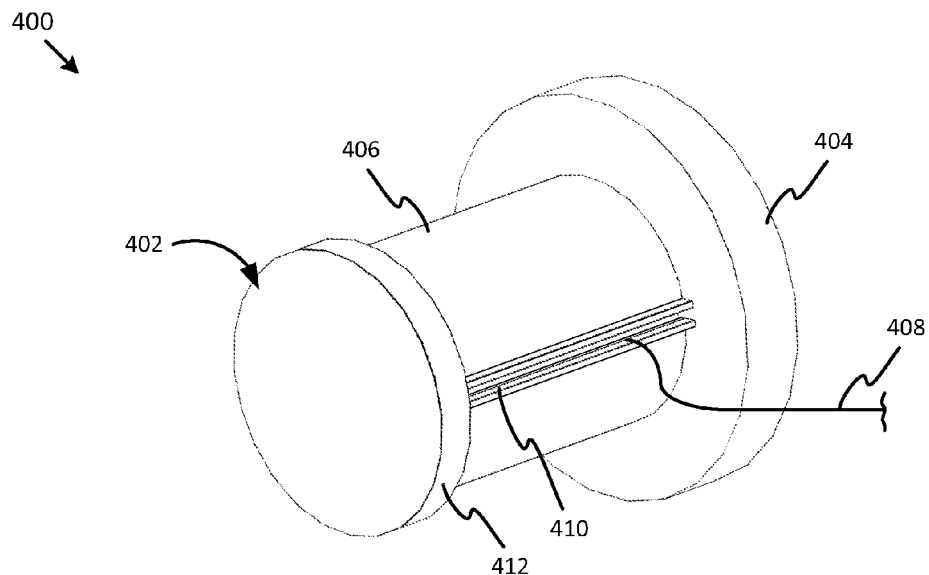
FIG. 5 is a diagrammatic illustration of an exemplary wire collection device for a stent delivery system with a retention clip.
Figure 6:
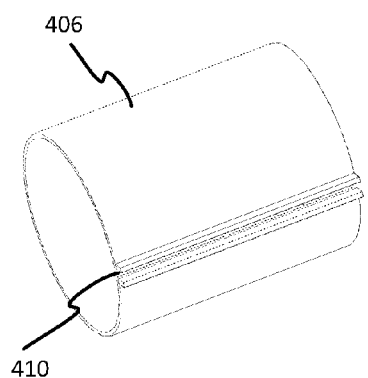
FIG. 6 is a diagrammatic illustration of a retention clip for an exemplary wire collection device for a stent delivery system.

In some embodiments, as illustrated with reference to FIGS. 5-6, the wire collection device 400 may include a collection spindle 402, a thumbwheel 404, and a retention clip 406. The collection spindle 402 may be any spindle, axle, or generally cylindrical structure around which a retraction wire is wound or collected, including, for example, the embodiments disclosed herein, such as collection spindles 114, 204, 304. The retention clip 406 is a cylinder with a C-shaped profile that is configured (e.g., sized and shaped) to fit around the outer diameter of the spindle 402 so as to maintain or guide the retraction wire 408 within spiral grooves (e.g., as shown in embodiments illustrated with reference to FIGS. 1-4) of the spindle 402. In some embodiments, the retention clip 406 may have any profile that surrounds the spindle 402 while maintaining the retraction wire 408 in the spiral grooves of the spindle 402. By preventing the retraction wire 408 from being misaligned from the spiral grooves during sheath retraction, the retention clip 408 may allow the wire collection device 400 to provide a smooth feel to the user. The retention clip 406 may rotate freely about the collection spindle 402, and the retraction wire 408 passes through a slot 410 of the retention clip 406 to the spindle 402. A shoulder 412 of the spindle 402 may keep the retention clip 406 in position. The retention clip 406 may extend partially or entirely across the height of spindle 402. The retention clip 406 may be made of flexible material with a smooth outer surface to allow the retraction wire 408 to slide across its surface.

Figure 7:
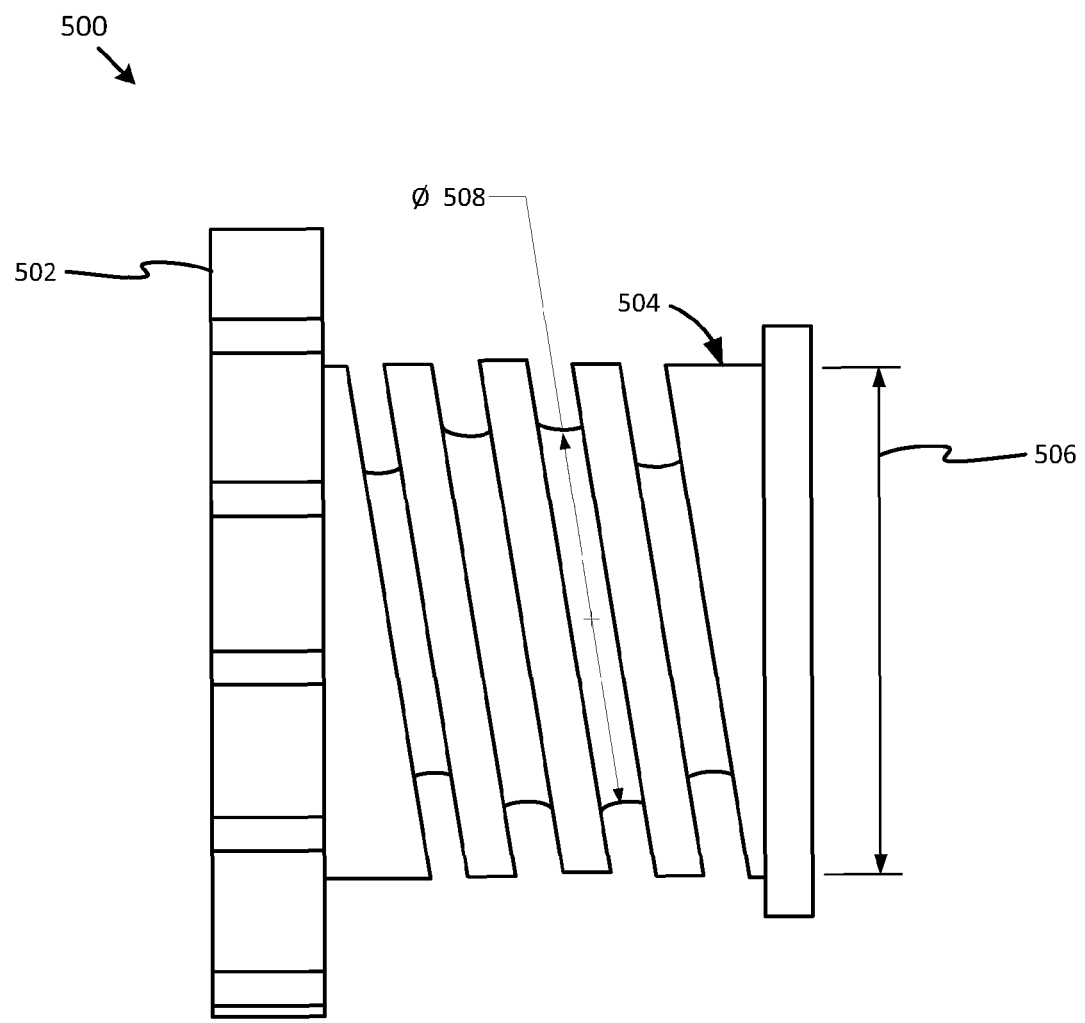
FIG. 7 is a diagrammatic illustration of an exemplary wire collection device for a stent delivery system.

In some embodiments, as illustrated with reference to FIGS. 7 and 8, the wire collection device has a varying collection diameter that increases and decreases along a non-linear profile. For example, as shown in FIG. 7, the wire collection device 500 includes a thumbwheel 502 and a collection spindle 504. The collection spindle 504 may have a substantially constant outer diameter 506 and varying collection diameter 508. The collection diameter 508 varies along a generally curvilinear shape, such as an ellipsoid or hyperboloid. The collection diameter 508 may increase along some portions of the spindle 502, and decrease along other portions.

Figure 8:
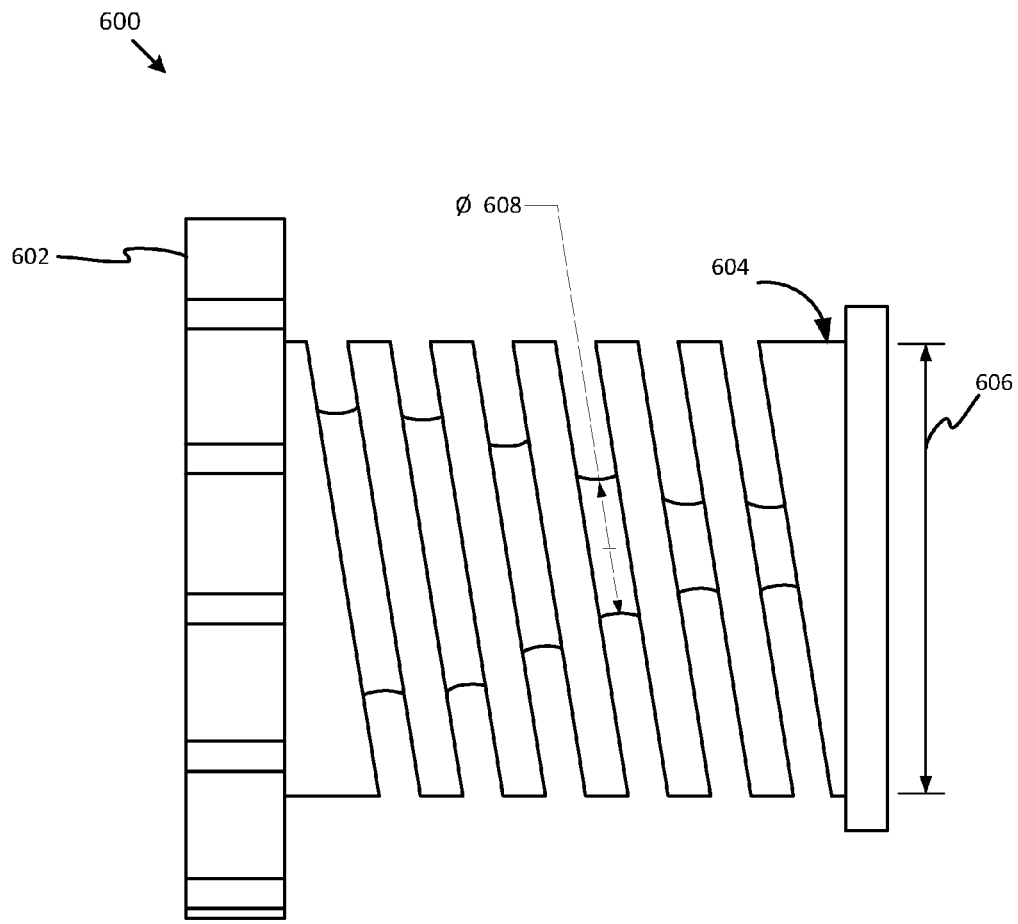
FIG. 8 is a diagrammatic illustration of an exemplary wire collection device for a stent delivery system.

With reference to FIG. 8, another example of the wire collection device 600 includes a thumbwheel 602 and a collection spindle 604. The collection spindle 604 may have a substantially constant outer diameter 606 and varying collection diameter 608. The collection diameter 608 varies along a generally non-linear shape, such as a stepped profile. The collection diameter 608 may increase along some portions of the spindle 602, and decrease along other portions. Those of skill in the art will appreciate that the collection spindle 602 may be configured so that the collection diameter 608 varies along profiles of other shapes, in order to accommodate the deployment force profile.

Figure 9:
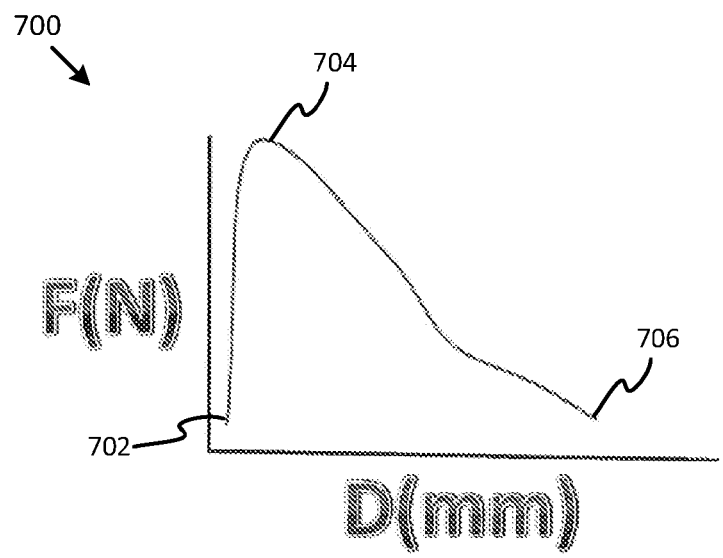
FIG. 9 is a required deployment force profile showing variation in required deployment force relative to stent deployment distance for a stent delivery system.

In some embodiments, for example, with reference to FIG. 9, a required deployment force profile 700 shows the required stent deployment force relative to the stent deployment distance (e.g., the distance of sheath retraction or length of retraction wire collected). In the depicted embodiment, the required deployment force increases from an initial force 702 to a threshold force 704, and decreases from the threshold force 704 to a lower force 706. The increase in required deployment force from the initial force 702 to the threshold force 704 may be the amount of force required to overcome the static friction and/or binding forces between a self-expanding stent and the outer sheath. Once the outer sheath begins to move, or retract, the required deployment force decreases from the threshold force 704 to the lower force 706, at the completion of sheath retraction.

In some embodiments, for example, with reference to FIG. 10, a profile 800 of the applied force, or the force required from the user to generate the required deployment force using a wire collection device as disclosed herein, may decrease from a maximum force 802 to a lower force 804. The difference, or variation, between the maximum force 802 and lower force 804 of the applied force is less than the difference, or variation, between the threshold force 704 and the lower force 706 of the required deployment force. The stent delivery system and wire collection device disclosed herein may reduce the rate of change of the applied force required to generate the required deployment force so as to provide to the user a smoother and more consistent the "touch and feel" during stent deployment. As shown in FIG. 10, the applied force/user-perceived force is substantially constant, particularly in comparison with the relative increase of deployment force being exerted (shown in FIG. 9).

Figure 11A:
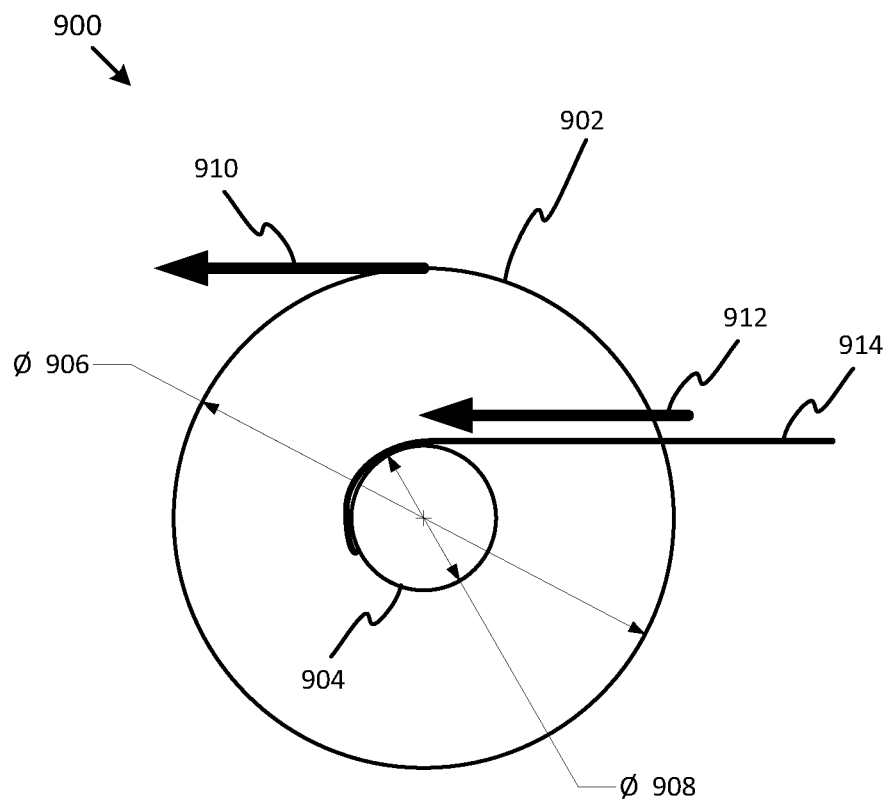
FIG. 11A is an exemplary schematic diagram showing forces acting on an exemplary wire collection device for a stent delivery system.

With reference to FIG. 11A, an exemplary schematic diagram of elements of a stent-deployment handle 900 is provided, showing a thumbwheel 902 and a spindle 904 that is coupled to the thumbwheel 902. The thumbwheel 902 has a diameter 906 and the spindle 904 has a collection diameter 908. As discussed above, the rotational axis of the collection diameter 908 may be aligned with the rotational axis of the thumbwheel 902, or the rotational axes may be offset. When a tangential force 910 is applied to the thumbwheel 902, such as by a thumb in flexion, it activates rotation of the spindle 904 such that a deployment force 912 (e.g., force required to retract the sheath at a given point in time) is applied to one or more retraction wires 914 coupled to the spindle 904 and that collect around the collection diameter 908. A single collection diameter is shown (while the constant outer diameter of the spindle referenced in the drawings and description above is not shown), but this should be understood as a representative snapshot at a given collection diameter value along the helical/increasing collection diameter such as is illustrated and described above (e.g., 118, 312, 314, 314, 508, 608). The torque T, in Newtons per meter (N/M), necessary to rotate the spindle 904 varies with the deployment force 912 (e.g., resistance between the sheath and the stent to be deployed) and the collection diameter 908. For example, the torque T may be estimated as $T = F_d \times (0.5 \times D_c)$, where $F_d$ is the deployment force 912, which varies as the sheath is retracted across the stent, and $D_c$ is the collection diameter 908. For a thumbwheel 902 with a diameter 906, the perceived thumb flexion force 910 varies with the torque T and the diameter 906 of the thumbwheel 902. For example, the perceived thumb flexion force 910 may be estimated as $F_r = T \div (0.5 \times D_c)$.

With reference to FIG. 11B, exemplary torque T values (in N/M) are provided for some embodiments of the wire collection device with varying collection diameter, for example, having a thumbwheel diameter 906 of 45 mm and deployment forces $F_d$ (in N) varying from 1 Newton to 34 Newtons and collection radii (in mm) at 8 mm, 9 mm, 10 mm, 11 mm, 12 mm, 13 mm, 14 mm and 20 mm. As can be seen, as the collection radius increases the amount of torque T also increases for the same amount of required deployment force $F_r$. In some embodiments, torque values under 0.11 N/M as shown in the Band A shaded area 1002 correspond with a perceived thumb flexion force 910 of up to about 5 Newtons; torque values of up to about 0.2 N/M in the Band B area 1004 correspond with a perceived thumb flexion force 910 of up to about 10 Newtons; and torque values above 0.2 N/M in the Band C shaded area 1006 correspond with a perceived thumb flexion force 910 of up to about 15 Newtons.

Although various embodiments of the invention have been described, it will be apparent to those of ordinary skill in the art that many more embodiments and implementations are possible that are within the scope of the invention. Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

I claim:

1. A stent delivery system including a wire collection device, the device comprising:
   a thumbwheel coupled to a collection spindle that is rotatable to collect a retraction wire about a varying collection diameter of the collection spindle, wherein:
   a proximal end of an outer stent-constraining sheath is coupled to the collection spindle by the retraction wire and a distal end of the outer stent-constraining sheath retractably surrounds a stent, the stent being a distally-disposed self-expanding stent;
   the collection spindle comprises an outer diameter being substantially constant and extending from a first end of the collection spindle to a second end of the collection spindle, the outer diameter being greater than the varying collection diameter, and the outer diameter having a surface receiving a retention clip; and
   the varying collection diameter increases from the first end of the collection spindle towards the second end of the collection spindle along a spiral groove formed between the varying collection diameter and the outer diameter in a manner that provides substantially constant rotating force on the thumbwheel, accommodating changing resistance as the outer stent-constraining sheath is retracted and releases binding force of the stent.

2. The system of claim 1, wherein a wall defining lateral sides of the spiral groove comprises a height that varies with the varying collection diameter and is equal to a difference between the outer diameter and the varying collection diameter.

3. The system of claim 2, wherein the wall of the spiral groove maintains the retraction wire within the spiral groove as the collection spindle is rotated to collect the retraction wire about the varying collection diameter.

4. The system of claim 1, wherein the thumbwheel is attached to the first end of the collection spindle, and a proximal end of the retraction wire is attached nearer the first end of the collection spindle, so that collection of the retraction wire begins nearer the first end of the collection spindle and ends nearer the second end of the collection spindle, and a ratio of outer stent-constraining sheath retraction distance to thumbwheel rotational displacement increases as the varying collection diameter increases.

5. The system of claim 1, wherein the thumbwheel is attached to the second end of the collection spindle, and a proximal end of the retraction wire is attached nearer the second end of the collection spindle, so that collection of the retraction wire begins nearer the second end of the collection spindle and ends nearer the first end of the collection spindle, and a ratio of outer stent-constraining sheath retraction distance to thumbwheel rotational displacement decreases as the varying collection diameter decreases.

6. The system of claim 1, wherein the thumbwheel further comprises a ratcheted extension that allows rotation of the thumbwheel in one direction, and prevents rotation of the thumbwheel in a reverse direction.

7. The system of claim 1, further comprising the retention clip, wherein the retention clip substantially surrounds the surface of the outer diameter of the collection spindle so as to maintain the retraction wire within the spiral groove as the collection spindle is rotated to collect the retraction wire about the varying collection diameter.

8. The system of claim 1, wherein the thumbwheel further comprises a grooved or notched surface that provides grip to a user.

9. The system of claim 1, wherein the varying collection diameter increases along a curvilinear profile from the first end of the collection spindle to the second end of the collection spindle.

10. The system of claim 1, wherein the varying collection diameter increases along a first portion of the collection spindle and decreases along a second portion of the collection spindle.

11. The system of claim 1, wherein the thumbwheel is axially offset from the collection spindle and coupled to the collection spindle by a transmission mechanism comprising mesh gears, a belt, a rack and pinion, a clutch, a ratchet, or any combination thereof.

12. A stent delivery system including a wire collection device, the device comprising:
   a first collection spindle coupled to a proximal end of an outer sheath by a first retraction wire, the first collection spindle rotatable to collect the first retraction wire about a first varying collection diameter of the first collection spindle;

a second collection spindle coupled to the proximal end of the outer sheath by a second retraction wire, the second collection spindle rotatable to collect the second retraction wire about a second varying collection diameter of the second collection spindle, and the second collection spindle being co-axial with respect to the first collection spindle; and a thumbwheel coupled between the first collection spindle and the second collection spindle and rotatable to control a retraction speed of the outer sheath by rotating the first collection spindle and the second collection, wherein at least one of the first collection spindle and the second collection spindle has an outer diameter with a surface receiving a retention clip.

13. The system of claim 12, wherein the first collection spindle and the second collection spindle each comprise the outer diameter, wherein the outer diameter is substantially constant, and wherein the outer diameter is greater than the first varying collection diameter and the second varying collection diameter.

14. The system of claim 13, wherein the first varying collection diameter increases, from a first end to a second end of the first collection spindle, along a first spiral groove formed between the first varying collection diameter and the outer diameter, and the second varying collection diameter increases, from a first end to a second end of the second collection spindle, along a second spiral groove formed between the second varying collection diameter and the outer diameter.

15. The system of claim 14, wherein:

a wall of the first spiral groove comprises a height that varies with the first varying collection diameter and is equal to a difference between the outer diameter and the first varying collection diameter; and a wall of the second spiral groove comprises a height that varies with the second varying collection diameter and is equal to a difference between the outer diameter and the second varying collection diameter.

16. The system of claim 15, wherein:

the wall of the first spiral groove maintains the first retraction wire within the first spiral groove as the first retraction wire collects about the first varying collection diameter; and the wall of the second spiral groove maintains the second retraction wire within the second spiral groove as the second retraction wire collects about the second varying collection diameter.

17. The system of claim 14, wherein the thumbwheel is attached at the first end of the first collection spindle and the first end of the second collection spindle.

18. The system of claim 17, wherein:

the first retraction wire is attached to the first collection spindle nearer the thumbwheel, so that collection of the first retraction wire begins nearer the first end of the first collection spindle and ends nearer the second end of the first collection spindle; and the second retraction wire is attached to the second collection spindle nearer the thumbwheel, so that collection of the second retraction wire begins nearer the first end of the second collection spindle and ends nearer the second end of the second collection spindle.

19. A wire collection device for a stent delivery system, the device comprising:

a pair of co-axial collection spindles coupled to a proximal end of an outer sheath by a pair of retraction wires, the collection spindles rotatable to collect the retraction wires about varying collection diameters of the collection spindles, wherein:

the pair of co-axial collection spindles comprise outer diameters that are substantially constant and that are greater than the varying collection diameters, wherein the outer diameters each include a surface that receives a retention clip, the varying collection diameters increase from a first end of each collection spindle to a free end of each collection spindle, the pair of retraction wires are coupled to the first end of each collection spindle, so that collection of the wires begin nearer the first end of each collection spindle and ends nearer the free end of each collection spindle; and a thumbwheel coupled between the collection spindles and rotatable to control a retraction speed of the outer sheath by actuating rotation of the collection spindles.

20. The device of claim 19, further comprising the retention clips positioned such that they respectively substantially surround the outer diameters of the pair of collection spindles so as to maintain the pair of retraction wires within spiral grooves as the collection spindles are rotated to collect the retraction wires about the varying collection diameters.

* * * * *